(12) United States Patent
Soscia et al.

(10) Patent No.: US 11,725,170 B2
(45) Date of Patent: Aug. 15, 2023

(54) SYSTEM AND METHOD FOR THREE-DIMENSIONAL IN VITRO FLEXIBLE MICROELECTRODE ARRAY

(71) Applicant: Lawrence Livermore National Security, LLC, Livermore, CA (US)

(72) Inventors: David Soscia, Livermore, CA (US); Heather Ann Enright, Livermore, CA (US); Nicholas Fischer, Livermore, CA (US); Doris Mailie Lam, Dublin, CA (US); Angela C. Tooker, Livermore, CA (US); Michael Triplett, Livermore, CA (US); Elizabeth K. Wheeler, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 411 days.

(21) Appl. No.: 16/677,328

(22) Filed: Nov. 7, 2019

(65) Prior Publication Data
US 2021/0139828 A1    May 13, 2021

(51) Int. Cl.
| | | |
|---|---|---|
| *C12M 1/32* | (2006.01) | |
| *C12N 5/00* | (2006.01) | |
| *C12M 1/42* | (2006.01) | |
| *B01L 3/00* | (2006.01) | |
| *G01N 27/30* | (2006.01) | |

(52) U.S. Cl.
CPC ........... *C12M 23/12* (2013.01); *B01L 3/5085* (2013.01); *C12M 35/02* (2013.01); *C12N 5/0068* (2013.01); *G01N 27/30* (2013.01); *B01L 2300/0829* (2013.01); *C12N 2513/00* (2013.01); *C12N 2539/00* (2013.01)

(58) Field of Classification Search
CPC ..... C12M 23/12; C12M 35/02; B01L 3/5085; B01L 2300/0829; C12N 5/0068; C12N 2513/00; C12N 2539/00; G01N 27/30

USPC ...................................................... 435/287.1
See application file for complete search history.

(56) References Cited

U.S. PATENT DOCUMENTS 8,101,401 B2 * 1/2012 Muller-Hartmann ................ C12M 23/12
435/285.2

OTHER PUBLICATIONS

Soscia et al., Controlled placement of multiple CNS cell populations to create complex neuronal cultures, PLOS ONE (Year: 2017).*
Chen et al., A three-dimensional flexible microprobe array for neural recording assembled through electrostatic actuation, Lab Chip, (Year: 2011).*
Takeuchi et al., 3D flexible multichannel neural probe array, Journal of Micromechanics and Microengineering (Year: 2003).*
Soscia, D., et al., "Controlled placement of multiple CNS cell populations to create complex neuronal cultures," PloS one, 2017, 12(11): p. e0188146.

(Continued)

*Primary Examiner* — Michael L Hobbs
*Assistant Examiner* — Lenora A Abel
(74) *Attorney, Agent, or Firm* — Harness, Dickey & Pierce, P.L.C.

(57) ABSTRACT

The present disclosure relates to a biocompatible, in vitro probe system. The probe system may have a substrate and a culture well supported on the substrate. The culture well defines a three-dimensional volume for containing in vitro cultures of electroactive cells. The probe system has at least one probe subsystem supported on the substrate. The probe subsystem has at least one probe having an array of electrodes, with the probe being disposed within the culture well for in vitro electrically communicating with the electroactive cells. The probe subsystem is adapted to be interfaced to an external instrumentation/recording device.

18 Claims, 7 Drawing Sheets

(56) References Cited

OTHER PUBLICATIONS

Chen, C.-H., et al., "A three-dimensional flexible microprobe array for neural recording assembled through electrostatic actuation," Lab on a Chip, 2011, 11(9): pp. 1647-1655.

Takeuchi, S., et al., "3D flexible multichannel neural probe array," Journal of micromechanics and microengineering, 2003, 14(1): p. 104).

Iwase, E., S. Takeuchi, and I. Shimoyama, "Sequential batch assembly of 3-D microstructures with elastic hinges by a magnetic field in Technical Digest, MEMS 2002 IEEE International Conference," Fifteenth IEEE International Conference on Micro Electro Mechanical Systems (Cat. No. 02CH37266) 2002; 7.

Zhou, T., et al., "Syringe-injectable mesh electronics integrate seamlessly with minimal chronic immune response in the brain," Proceedings of the National Academy of Sciences, 2017, 114(23): pp. 5894-5899.

Tian, B., et al., "Macroporous nanowire nanoelectronic scaffolds for synthetic tissues," Nature materials, 2012, 11(11): p. 986.

Kireev, D., et al., "N3-MEA Probes: Scooping Neuronal Networks, Frontiers in Neuroscience," 2019, 13(320).

Heuschkel, M.O., et al., "A three-dimensional multi-electrode array for multi-site stimulation and recording in acute brain slices," Journal of neuroscience methods, 2002, 114(2): pp. 135-148).

In vivo Utah Array (Charvet, G., et al., "BioMEA™: A versatile high-density 3D microelectrode array system using integrated electronics," Biosensors and Bioelectronics, 2010. 25(8): pp. 1889-1896.

\* cited by examiner

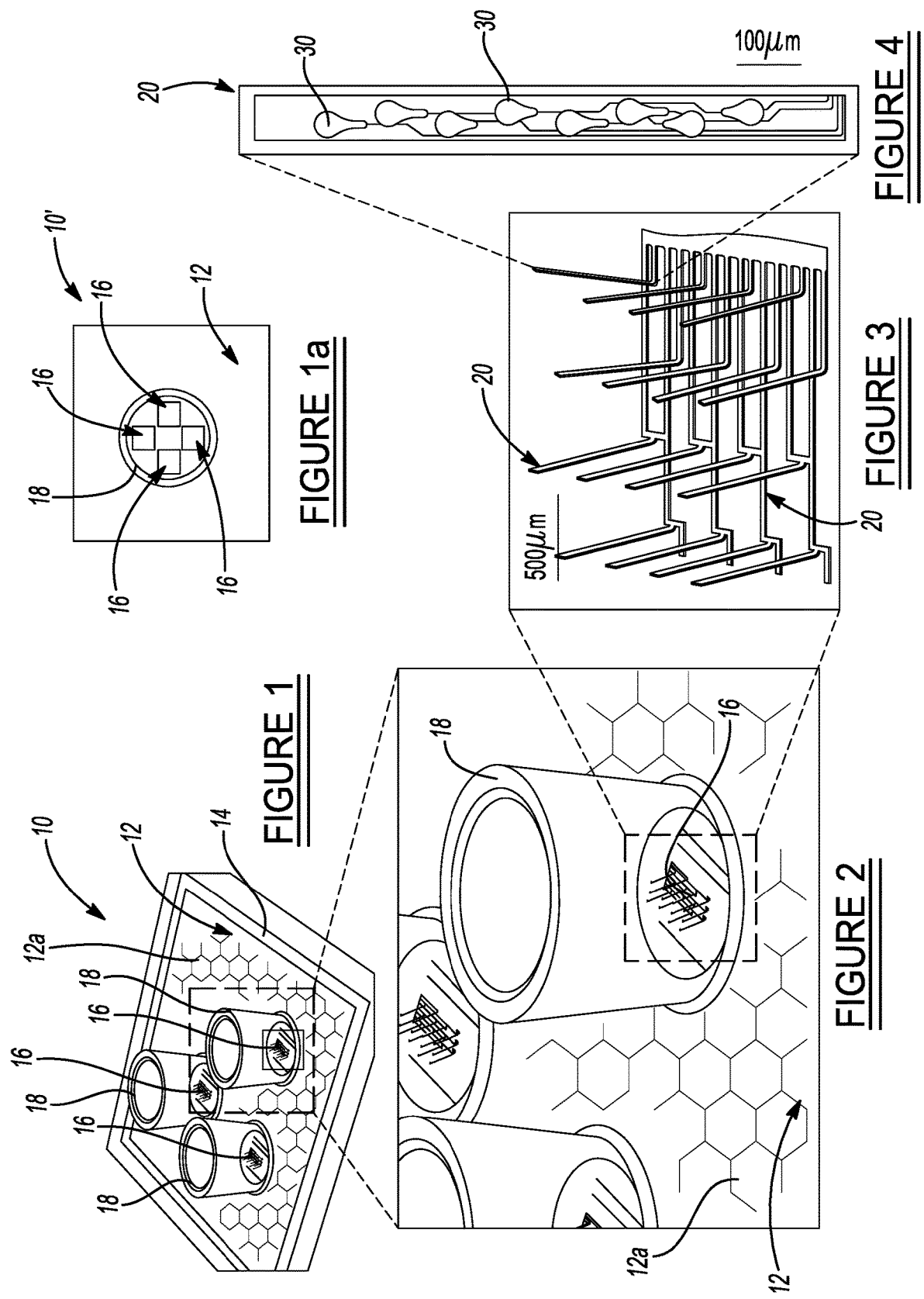

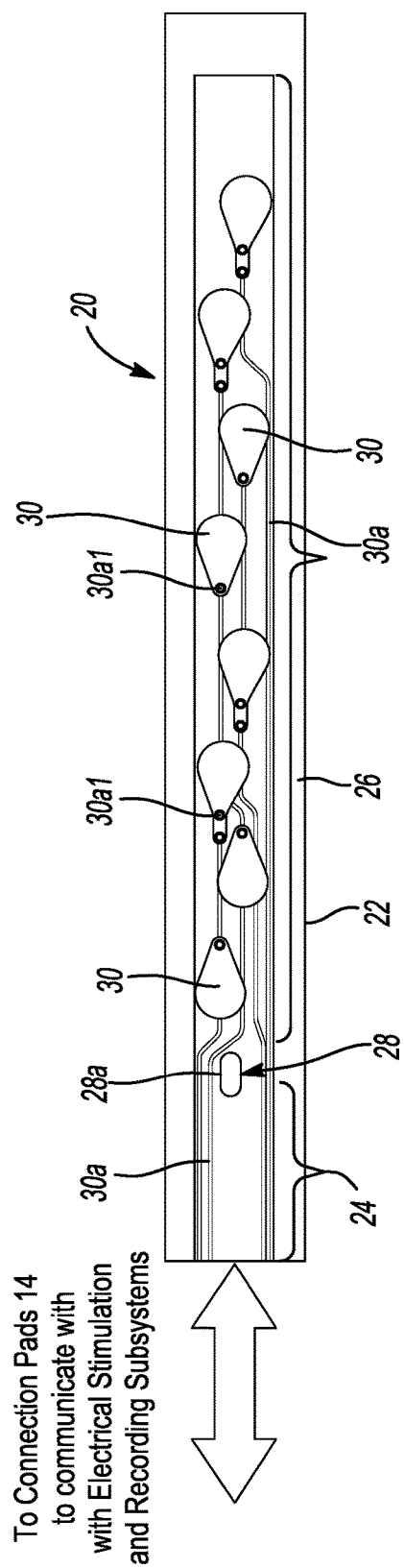
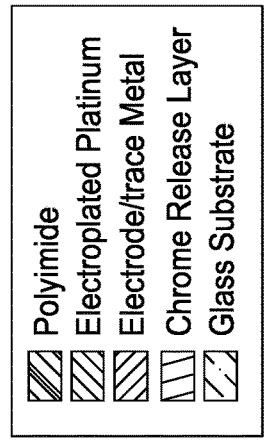
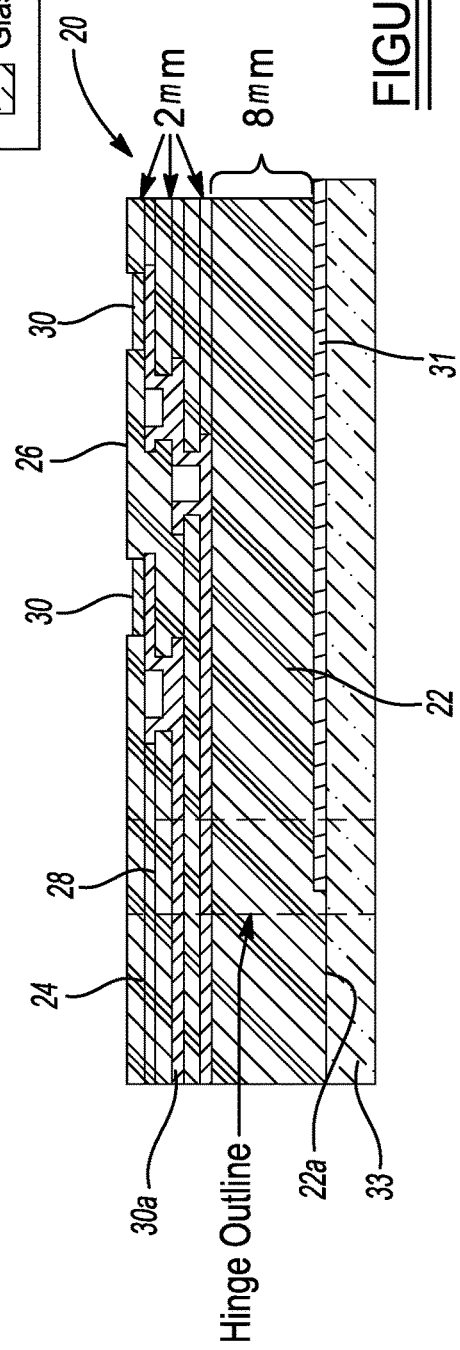
FIGURE 5
FIGURE 5a

SYSTEM AND METHOD FOR THREE-DIMENSIONAL IN VITRO FLEXIBLE MICROELECTRODE ARRAY

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to biocompatible probe systems, and more particularly to a three-dimensional, biocompatible, in vitro probe system which provides a plurality of probes arranged to extend within a three-dimensional volume of a culture of cells comprised of at least one electroactive cell, enabling the electrical stimulating of the electroactive cells contained within the culture well or the recording of electrical signals from the electroactive cells.

BACKGROUND

The statements in this section merely provide background information related to the present disclosure and may not constitute prior art.

A 3D in vitro platform containing electroactive cells such as neurons more closely resembles the complex organization of in vivo human organs such as the brain as compared to traditional 2D cultures, and thus can provide more accurate organ models to study disease, chemical exposures, or develop new drugs or medical countermeasures to chemical or biological agents. Electrophysiological recordings of electroactive cells are a common and trusted method of non-invasively evaluating health, network communication, and response to chemical insults. Action potentials, the fundamental unit of electrophysiological communication between electroactive cells, are generally monitored in vitro using electrodes that record these events by measuring a change in transmembrane or extracellular voltage. For cells cultured in 2D, measuring these events is often achieved through a microelectrode array (MEA) consisting of several thin-film metal electrodes patterned on the cell growth substrate. There are currently limited options, however, for interrogating many locations simultaneously throughout a 3D network of electroactive cells in vitro due to engineering challenges associated with fabricating an MEA in 3D space. As a result, most 3D cultures utilize traditional single electrodes made from glass or metals that are inserted into the 3D cell-containing matrix after the culture is established. Employing these methods risks damage to the cell network and supporting structure and provides no means of evaluating network communication across multiple locations. And although multiple electrodes can be used, they often contain bulky support/handling structures that make it difficult to place more than a few into a cell culture well, and equally difficult to accurately or reproducibly target specific locations within the 3D matrix of cells.

In other studies, 2D arrays of electrodes have been extended from substrates to measure a single plane of neurons. These generally are in the form of "spike" electrode arrays similar to the in vivo Utah Array (Charvet, G., et al., "BioMEA™: A versatile high-density 3D microelectrode array system using integrated electronics," Biosensors and Bioelectronics, 2010. 25(8): pp. 1889-1896; Heuschkel, M. O., et al., "A three-dimensional multi-electrode array for multi-site stimulation and recording in acute brain slices," Journal of neuroscience methods, 2002, 114(2): pp. 135-148). More recently, a new style of MEA has also been introduced, using a flexible polymer "mesh" containing either nanowire or thin-film electrodes (Kireev, D., et al., "N3-MEA Probes: Scooping Neuronal Networks, Frontiers in Neuroscience," 2019, 13(320); Tian, B., et al., "Macroporous nanowire nanoelectronic scaffolds for synthetic tissues," Nature materials, 2012, 11(11): p. 986; Zhou, T., et al., "Syringe-injectable mesh electronics integrate seamlessly with minimal chronic immune response in the brain," Proceedings of the National Academy of Sciences, 2017, 114(23): pp. 5894-5899). As they are extremely flexible and not integrated into a device, they require support structures to allow handling and lack the ability to precisely position electrodes in 3D space. Additionally, to capture recordings from more than one plane of cells in a 3D matrix, meshes need to be layered on top of one another or folded or rolled, further complicating handling and positioning. These approaches have been mostly focused on in vivo or ex vivo tissue-based applications, but can also be used for vitro cell cultures.

Two groups have published work on flexible multi-electrode, multi-probe arrays that are actuated from their initial configuration. Iwase and Takeuchi published papers in 2002 and 2003 from The University of Tokyo, respectively, detailing probes with embedded ferromagnetic backbones to actuate with an external magnetic field (Iwase, E., S. Takeuchi, and I. Shimoyama, "Sequential batch assembly of 3-D microstructures with elastic hinges by a magnetic field in Technical Digest, MEMS 2002 IEEE International Conference," Fifteenth IEEE International Conference on Micro Electro Mechanical Systems (Cat. No. 02CH37266) 2002; 7. Takeuchi, S., et al., "3D flexible multichannel neural probe array," Journal of micromechanics and microengineering, 2003, 14(1): p. 104). These were intended for in vivo applications and have practical limitations in that the ferromagnetic component significantly stiffens the polymer-based probes and introduces potentially cytotoxic materials. Additionally, there is no method of fixing the probes in place once they are actuated using the magnetic field.

Chen published a paper in 2011 (Chen, C.-H., et al., "A three-dimensional flexible microprobe array for neural recording assembled through electrostatic actuation," Lab on a Chip, 2011, 11(9): pp. 1647-1655) that was later patented in 2012 describing flexible microelectrode probes actuated by external electrostatic forces.

SUMMARY

This section provides a general summary of the disclosure, and is not a comprehensive disclosure of its full scope or all of its features.

In one aspect the present disclosure relates to a biocompatible, in vitro probe system. The system may comprise a substrate; a culture well supported on the substrate and defining a three-dimensional volume for containing in vitro cultures of electroactive cells; and at least one probe subsystem. The probe subsystem may be supported on the substrate and may include at least one probe having an array of electrodes disposed within the culture well for in vitro electrically communicating with the electroactive cells, and adapted to be interfaced to an external electronic instrumentation/recording device.

In another aspect, the present disclosure relates to a biocompatible, in vitro probe system. The system may comprise a generally planar substrate; a culture well secured to a surface of the substrate and defining a three-dimensional volume for containing in vitro cultures of electroactive cells; and at least one probe subsystem supported on the substrate and including a first region and a second region. The second region may include a plurality of probes arranged in the X-Y plane extending non-parallel to the first region, and disposed inside the three-dimensional volume of the culture well. At least a portion of the first region extends parallel to the substrate and out from the culture well. Each of the probes includes a plurality of spaced apart electrodes that collectively form an in vitro, three-dimensional network of electrodes within the three-dimensional volume of the culture well. The probe subsystem further includes circuit traces extending from the first region into the second region and into electrical contact with the electrodes of each of the probes, for enabling an external electrical subsystem to electrically communicate with the electrodes on the probes.

In still another aspect the present disclosure relates to a method for electrically communicating with a quantity of cultures of electroactive cells. The method may comprise using a culture well to define a three-dimensional volume for containing in vitro cultures of electroactive cells. The method may further include using at least one probe subsystem having a portion with a plurality of probes extending into the culture wells, wherein each said probe includes a plurality of electrodes, to form a three-dimensional network of electrodes within the three-dimensional volume of the culture well. The method may further include using the electrodes to in vitro electrically communicate with the electroactive cells.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings, in which:

FIG. 1 is a perspective view of one embodiment of a biocompatible, in vitro flexible microelectrode array system with three independent multi-electrode arrays in separate culture wells, in accordance with one embodiment of the present disclosure;

FIG. 1a is a top plan view of another embodiment of the system of the present disclosure which makes use of a plurality of probe subsystems associated with a one culture well;

FIG. 2 is an enlarged perspective view of one of the culture wells shown in FIG. 1;

FIG. 3 is a highly enlarged perspective view of the probe array of one of the probe subsystems of the system of FIG. 1;

FIG. 4 is a highly enlarged plan view of one of the probes;

FIG. 5 is an enlarged top plan view of one of the probe subsystems showing the probe of FIG. 4 with the electrodes arranged generally in a substantially straight longitudinal line, and showing three distinct regions of the probe subsystem;

FIG. 5a is a side cross sectional side view of a portion of the probe of FIG. 5 showing the various electrical traces arranged at different depths with the probe substrate material;

DETAILED DESCRIPTION

Figure 6:
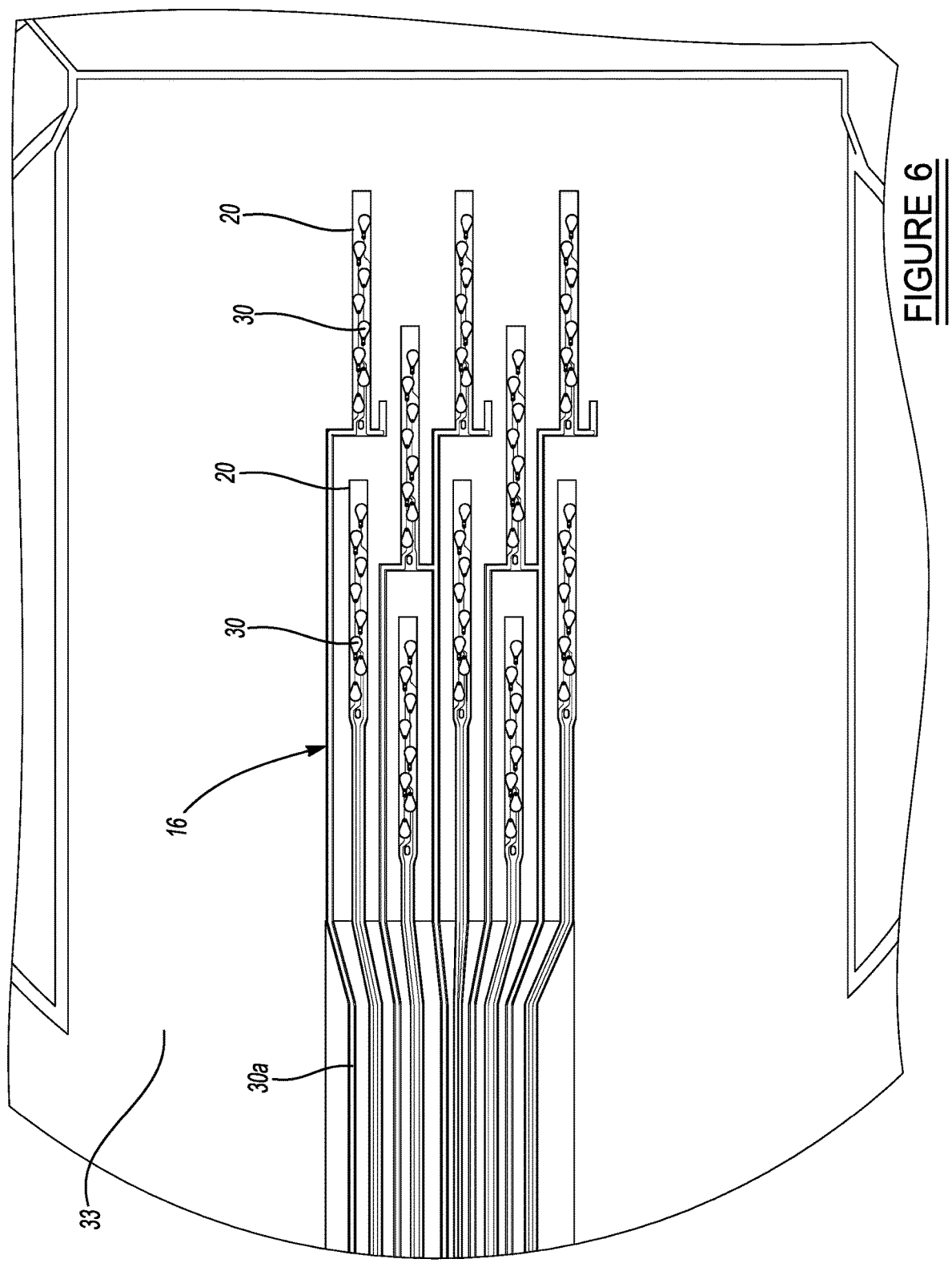
FIG. 6 is a top plan view of one probe subsystem showing its probes arranged generally flat prior to be actuated into the shape shown in FIG. 3.

Example embodiments will now be described more fully with reference to the accompanying drawings.

Referring to FIG. 1, one embodiment of a biocompatible, in vitro probe system 10 in accordance with the present disclosure is shown. The system 10 in this embodiment includes a substrate 12 having an upper surface 12a, a plurality of electrical connection pads 14 arranged on the upper surface 12a around a perimeter of the upper surface, at least one probe subsystem 16 supported on the upper surface, and at least one culture well 18 secured to the upper surface 12a. The culture well 18 is intended to hold cultures of electroactive cells and potentially also other cell types. In the system 10 shown in FIG. 1, three probe subsystems 16 and three culture wells 18 are incorporated, but a greater or lesser number of probe subsystems and associated culture wells may be used to meet the needs of a specific application. Furthermore, as shown in FIG. 1a, a probe system 10' may be constructed which incorporates a plurality of probe systems 16 associated with a single culture well 18. Other configurations are just as readily able to be constructed, and the present disclosure is therefore not limited to just one probe subsystem 16 being used with just one culture well 18.

As shown further in FIGS. 2 and 3, the probe subsystem 16 includes an array of independent probes 20 that are located within the 3D volume of the culture well 18. The probes 20 in this example form a rectangular arrangement of probes with distinct rows and columns. As will be described more fully in the following paragraphs, the row and column arrangement of the probes 20 enables a 3D array of microelectrodes to be provided in X, Y and Z axes within the culture cell 18 once the probes 20 are arranged vertically within the culture cell 18. The culture cell 18 is secured with a fluid-tight seal to the upper surface 12a of the substrate 12. One suitable (i.e., biocompatible) epoxy for performing this attachment is EPO-TEK® 301-2 epoxy, available from Epoxy Technology of Billerica, Mass. The culture well 18 may be formed from glass, plastic, or any other suitable material which is biocompatible. Prior to securing of the culture well, each array is temporarily protected from outgassing from the epoxy with a polycarbonate/PDMS cylinder placed over the probe array but inside the inner diameter of the culture well.

While a row/column arrangement of the probes 20 is shown in FIG. 3, the probes 20 may be arranged in virtually any configuration, for example in concentric circles, concentric squares, etc. Also, the culture well 18, while shown as having a round shape, could just as readily be formed with a square shape, a rectangular shape, or virtually any other shape to meet a specific application. The 3D shape of the culture well 18 will in many instances have a large bearing on the optimal configuration of the probes 20.

FIG. 4 shows one of the probes 20 in greater detail. The probe 20 includes a plurality of microelectrodes 30 (hereinafter simply "electrodes 30") spaced along a length thereof, generally in a substantially straight line. However, this is but one example and the electrodes 30 could be arranged in different configurations (e.g., two or more parallel or non-parallel paths). Each electrode 30 of each probe 20 may be used to receive electrical signals from electroactive cells contained in the culture well 18, or to apply electrical stimulation to the electroactive cells. The probes 20 can be configured such that certain ones of the probes apply electrical stimulation while others record electrical signals, or any given electrode(s) 30 can potentially be controlled so as to be used alternately for these two operations.

FIG. 5 shows a major portion of the probe 20 in greater detail. The probe 20 includes a planar probe body portion 22 (which may be viewed as a "substrate") which may be formed from a polymer, which in one example is polyimide. A first region 24 of the probe body 22 is used to secure the probe subsystem 16 to the upper surface 12a of the substrate. A second region 26 carries the electrodes 30 and forms the sensing body portion of the probe. A hinge region 28 contains a void 28a which mechanically weakens the hinge region 28 and allows preferential bending in this region, enabling the second region 26 to be readily buckled and lifted into the orientation shown in FIG. 3. As will be discussed further below, the probes 20 are actuated such that plastic deformation of the polymer of the probe body 22 in the hinge region 28 occurs, allowing the second regions 26 of the probes 20 to remain actuated (i.e., in their substantially vertical positions) without requiring any fixing element or external force after the initial mechanical actuation process is completed.

Each electrode 30a is connected to at least one circuit trace 30a via at least one metal via 30a1. All of the circuit traces 30a lead out through the first region 24 (i.e., out from the interior volume of the culture well 18) and extend through an interior area of the substrate 12 (or alternatively on the upper surface 12a of the substrate) to the electrical connection pads 14. This enables independent electrical connections between the electrodes 30 and separate ones of the electrical connection pads 14, such that each electrode 30 communicates with a single associated one of the electrical connection pads 14. Optionally, certain groups of electrodes 30 could be configured (e.g., in parallel) to communicate with one or more ones of the electrical connection pads 14. The form factor of the system 10 enables the electrodes 30 to be quickly and easily placed in communication with external electrophysiological stimulation and/or instrumentation/recording hardware devices (not shown) via the electrical connection pads 14.

The electrodes 30 may be made of any suitable electrically conductive material, but biocompatible metals such as gold, platinum, titanium, iridium, or a combination of such multiple metals, is preferred. In one specific implementation, the probes 30 are each formed from gold and electroplated with platinum. The surfaces of the electrodes 30 can be further coated with other metals, polymers, or biomolecules to increase performance, biocompatibility or functionality of the electrodes. For example, electroplating of a rough metal film can decrease impedance and increase signal-to-noise ratio of the electrodes 30 during electrical recordings. Prior to actuation, platinum black was electroplated for 2.5 minutes using a constant voltage of −30 mV to increase biocompatibility and signal-to-noise ratio of the electrodes during electrophysiological recordings. A solution of 192 mg/l hexachloroplatinate IV hexahydrate in 0.1M nitric acid was used. The plating parameters used were less aggressive than previously reported (Soscia, D., et al., "Controlled placement of multiple CNS cell populations to create complex neuronal cultures," PloS one, 2017, 12(11): p. e0188146) to eliminate the possibility of the Pt film cracking or delaminating during probe actuation. The electrodes 30 can be used for electrophysiological recording, stimulation, or detection of chemical compounds if functionalized with additional suitable coatings.

FIG. 5a shows a cross-sectional side view of a portion of the probe 20 to illustrate how the electrical traces 30a may be formed within the probe body 22 polymer material in a vertically spaced arrangement. This enables connections to the electrodes 30. A metal release layer (e.g., chrome, aluminum, etc.) 31 may be used on a lower surface 22a of the probe body 22, which permits the second region 26 to be buckled and lifted from a glass substrate 33, relative to the first region 24, during actuation (i.e., manufacturing) of the probe 20.

During construction of a working prototype of the probe system 10 by the co-inventors, the probes 20 were fabricated using wafer-level cleanroom processing. First, a chrome release layer was patterned on 6" Borofloat-33 glass wafers (University Wafer, South Boston, Mass.) using wet etching. Eight μm of polyimide (HD Microsystems, Parlin, N.J.) was then deposited and cured. Next, the first metal layer of 20 nm Ti/250 nm Au/20 nm Ti was patterned via wet etching followed by deposition of 2 μm of polyimide. After defining interconnection vias, this process was repeated for a second trace metal layer. After an additional interconnection layer, an electrode metal layer of 20 nm Ti/250 nm Au was then patterned using a wet etch process. A final 2 μm layer of polyimide was added, connection pad and electrode vias were defined, and a device via etch to the substrate was performed on the polyimide. All polyimide etching was done using dry oxygen plasma. The wafers were then diced into individual chips, then immersed in CR-7 chrome etchant (Transene, Danvers, Mass.) for 5 hours at room temperature until the release layer was fully dissolved away.

Figure 7:
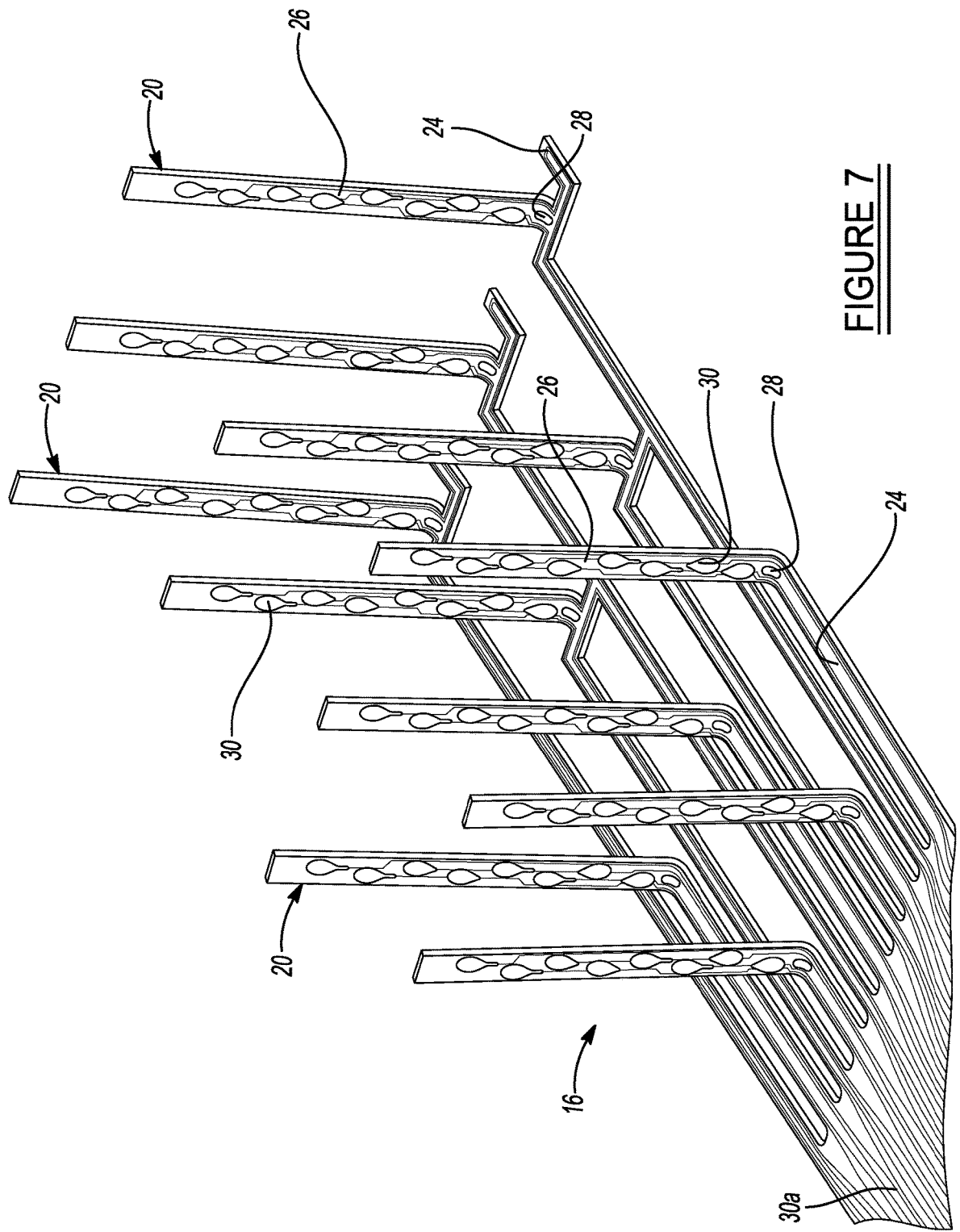
FIG. 7 is a highly enlarged perspective illustration of the X-Y-Z 3-dimensional grid-like array that the probes of a single probe subsystem form once actuated.

FIG. 6 shows one of the probe subsystems 16 with its associated probes 20 in a planar configuration prior to the buckling and actuation operations. It can be seen that the probes 20 are arranged in a staggered, branched or "tree-like" configuration on a glass substrate 33 which permits constructing a greater number of the probes 20 as the overall length of the probe is increased. However, other branching patterns or arrangements are possible as well to meet the needs of a specific application. FIG. 7 shows an enlarged perspective view of the probes 20 of one of the probe subsystems 16 after the probes have been buckled and fully lifted (actuated) into their final orientations. In this example the second regions 26 of each of the probes 20 extend generally perpendicular to the substrate 12 when the probe subsystem 16 is secured to the substrate 12. The second regions 26 of the probes 20 are spaced from one another in a somewhat grid-like pattern, and the electrodes 30 of each probe 20 are vertically spaced from one another and thus reside at different elevational levels within the 3D volume defined by the culture well 18, and effectively form a 3D network of precisely spaced electrodes. The second regions 26 of the probes 20, which essentially form the finished probe 20 "body", define the portion of each probe that extends vertically in this example, are all the same length, but they need not necessarily all be the same vertical length. A configuration where a first subplurality of the probes 20 are provided with a different vertical length from a second subplurality of the probes is also possible.

FIGS. 8-11 show the buckling and actuation operations performed to bend each of the probes 20 into their upright orientations as shown in FIG. 7. For this purpose commercially available micro-positioning machines are available from Newport Corp. of Irvine, Calif., Thorlabs Inc. of Newton, N.J., AZoNetwork of Manchester, UK and other companies. However, a custom apparatus was constructed by the engineers of the assignee of the present disclosure for the purpose of buckling and lifting the probes 20. These types of micro-positioning machines generally include elements which are able to apply highly controlled and repeatable forces along precise, desired axes of movement, and typically on a scale of a few micrometers to 10 s of millimeters in distance.

Figure 8:
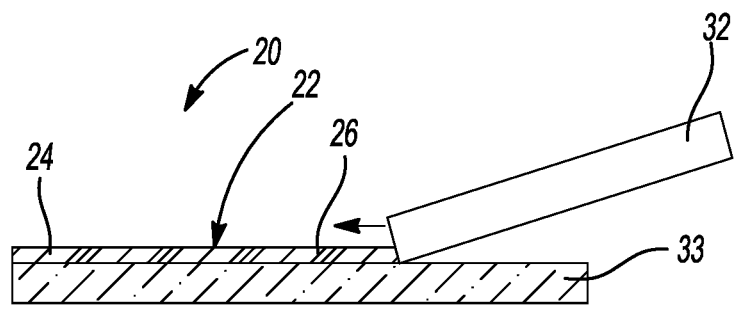
FIGS. 8-11 show simplified side view illustrations of one of the probes being buckled and lifted into the orientation shown in FIG. 7.
Figure 9:
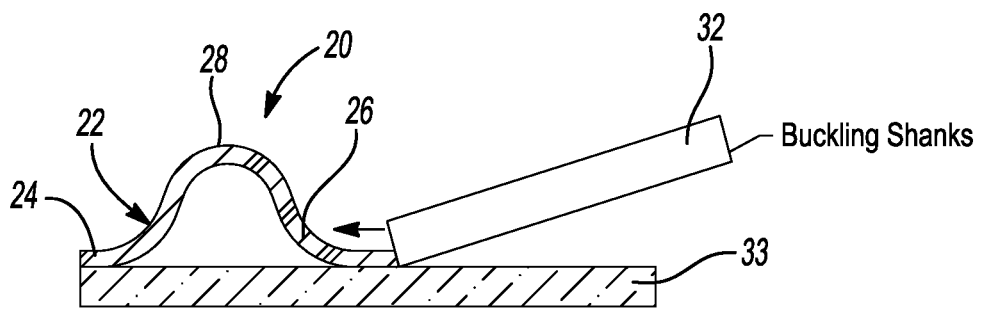
Figure 10:
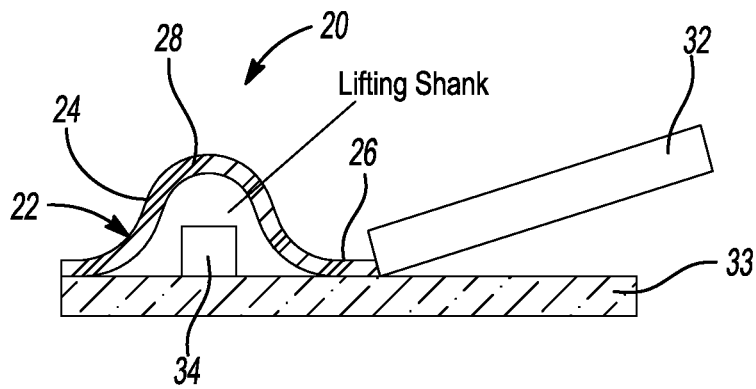
Figure 11:
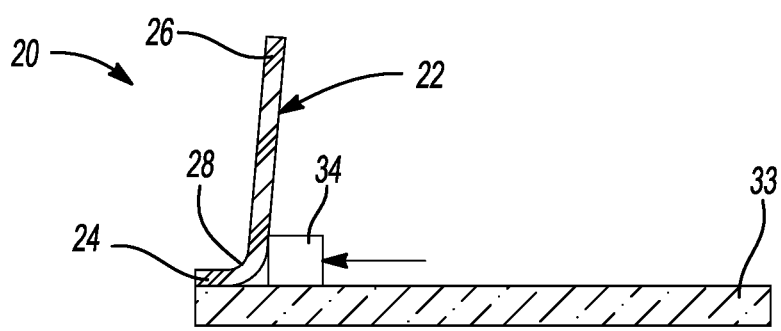
Figure 12A:
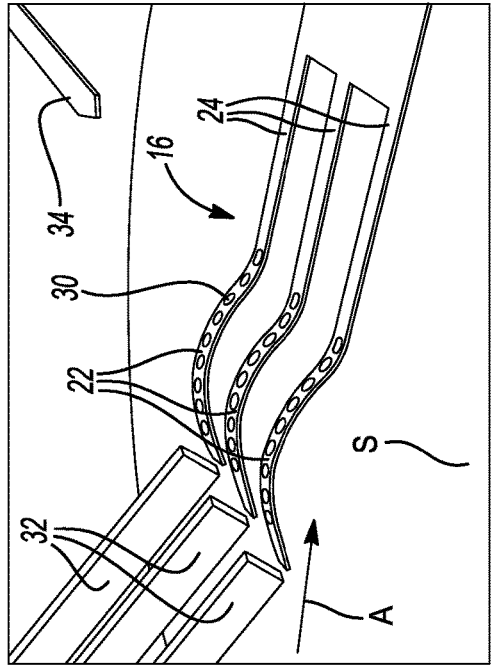
FIGS. 12a-12d show a micro-positioning device being used to simultaneously buckle a plurality of the probes, and then simultaneously lift the plurality of probes into their final configuration.
Figure 12B:
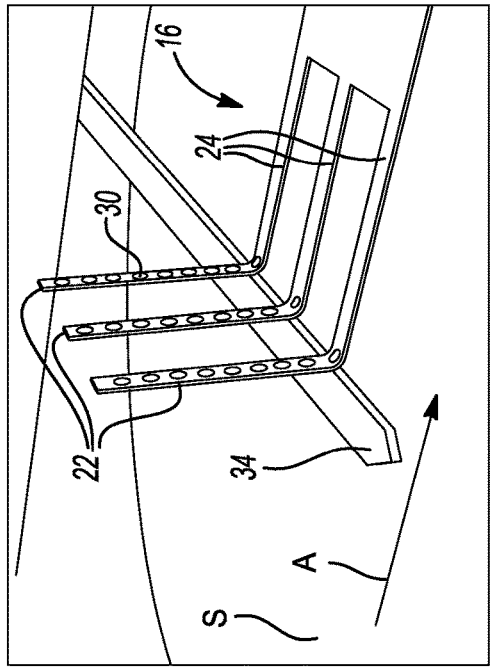
Figure 12C:
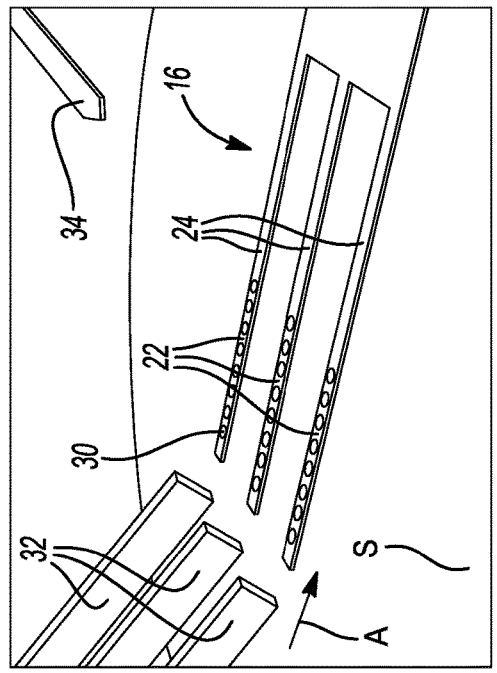
Figure 12D:
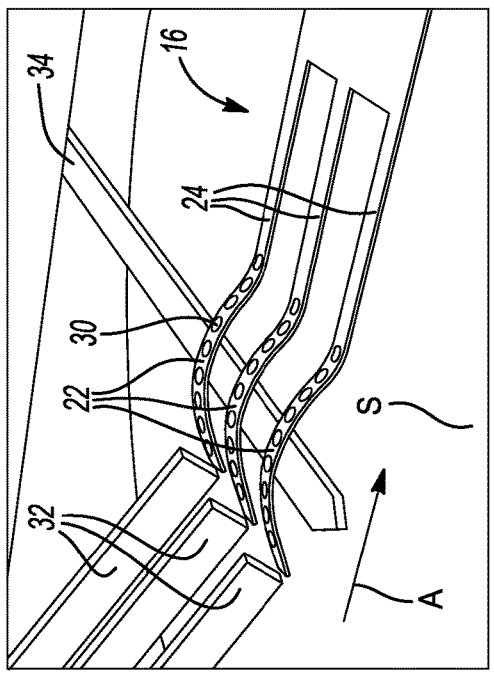

In FIGS. 8-10, a buckling shank 32 of such a micro-positioning machine is positioned at a free edge of each second region 26 of each probe 20 and used to apply a controlled, linear pushing force towards the bending region 28. This causes each probe 20 to "buckle," or arch, at its bending region 28. During this phase of construction the first region 24 remains secured to the glass substrate 33. The second region 26 is released from the substrate 33 when the chrome release layer 31 is dissolved away. This process is done before actuation and thus allows the buckling/lifting of the second region 26 from the glass substrate 33 during actuation. The actuation is achieved by controllably buckling the probes 20 (and more specifically the probe bodies 22) off the glass substrate 33 surface into an arched configuration using the buckling shanks 32, and then lifting the second regions 26 of the probes 20 into their final position (shown in FIG. 7) with lifting shanks 34, as shown in FIGS. 10 and 11. The lifting shanks 34 are elongated elements associated with the micro-positioning device which are also moved linearly toward the bending region 28. The lifting shanks 34 can perform the lifting step by either moving the second region 26 of each probe 20 horizontally relative to the glass substrate 33 toward the hinge region 28, moving them vertically away from the glass substrate 33, or a combination of both.

Briefly, shank designs were lithographically patterned on 250 μm-thick Si wafers for buckling shanks 32, and silicon-on-insulator (SOI) wafers with 100 μm-thick device layers for lifting shanks 34 (University Wafer, South Boston, Mass.). The silicon was then etched using a DRIE process. For buckling shanks 32, the shanks were released from a backing wafer using PRS2000 resist stripper (Fischer Scientific, Hampton, N.H.). For lifting shanks 34, the shanks were immersed in 49% hydrofluoric acid for 3 days for release. To limit probe damage during actuation, all silicon shanks 32 and 34 were uniformly coated with a 3.5 μm-thick Parylene C layer by vapor deposition.

In one embodiment of the probes 20, the final probe thickness was ~15 μm. The 8 μm base polyimide layer thickness was chosen to prevent damage to subsequent functional metal layers during the "lifting" phase of actuation of the probes. Additionally, this thickness allows both of the subsequent trace metal layers running through the hinge region 28 to be in mechanical compression during actuation since they are located above the neutral plane at ~7.5 μm, thus limiting the risk of trace breakage during this step.

As shown in FIGS. 12a-12d, the buckling shanks 32 may be micro-fabricated for precise actuation of multiple probes 20 simultaneously. To enable extremely fine placement accuracy relative to the probes 20, an actuating/positioning apparatus containing microdrives, such as available from Newport Corp., Thorlabs Inc., and AZoNetwork mentioned above, can be used to precisely, simultaneously move the buckling shanks 32 along direction "A" in FIGS. 12a-12c. The shanks 32 can each be a larger, cruder object such as a needle, for independently actuating a single probe 20. If a larger object such as a needle is used, the buckling step is optional, as the needle works to get under an end of the probe and essentially just lift it, without performing any buckling.

Figure 13:
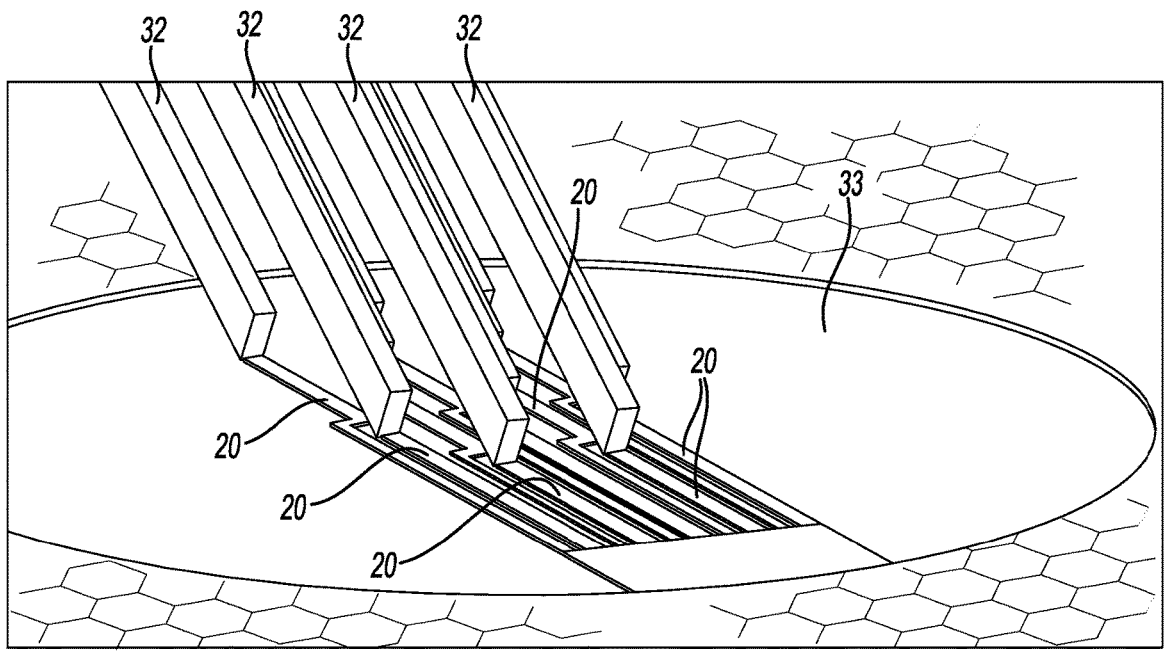
FIG. 13 shows elements of the micro-positioning device in position to simultaneously buckle a plurality of the probes.
Figure 14:
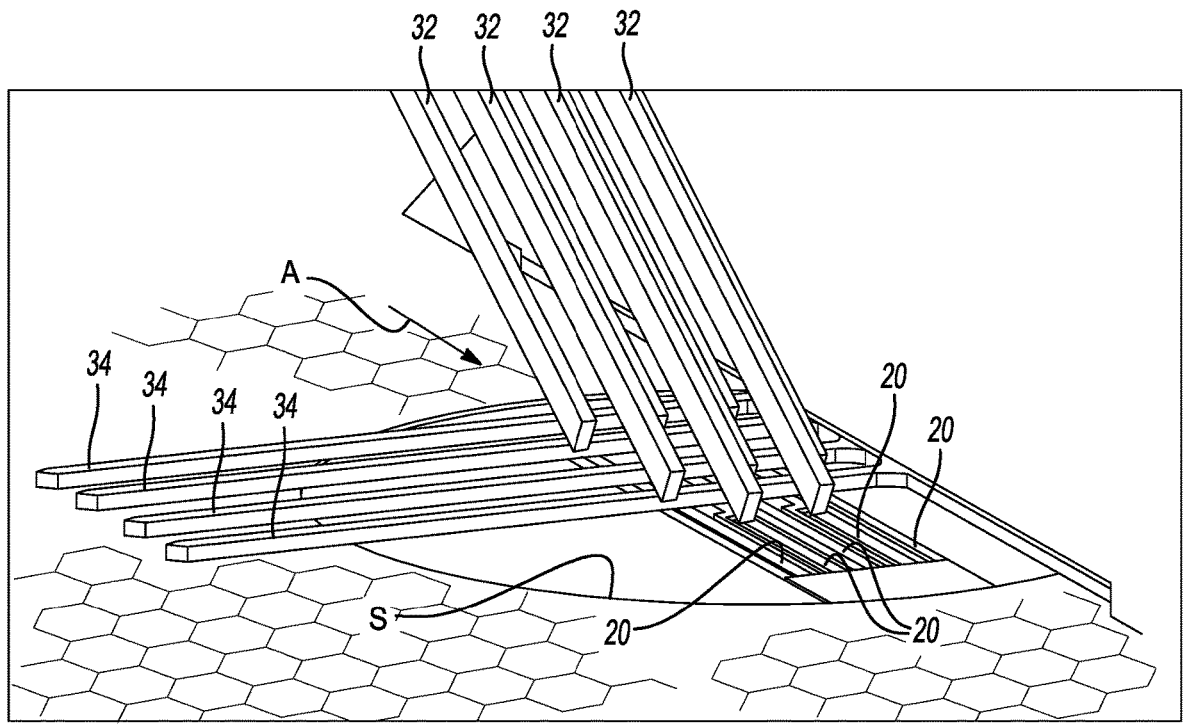
FIG. 14 shows elements of the micro-positioning tool in position to both buckle and lift a plurality of probes.

FIG. 13 shows a perspective view of the buckling shanks 32 in position and about to apply a buckling force to a plurality of the probes 20 simultaneously. FIG. 14 shows a plurality of the buckling shanks 32 in relation to lifting shanks 34 and the probes 20. At this point in the process, the probes will be in an arched formation with the lifting shanks 34 under them and each buckling shank 32 in contact with a single probe 20. However, in this conceptual model the probes 20 are shown in their flat planar orientation so they are not obstructing the view of the positional relationship between the buckling shanks 32 and lifting shanks 34. After this step in the process, the buckling shanks 32 would be retracted upward and/or at an angle away from the probes 20, allowing the probes 20 to straighten and lay over the lifting shanks 34 before being lifted vertically.

The length, width, thickness, number, and position of the array of probes 20 of each 3D probe subsystem 16 can be customized for specific applications, as they are preferably fabricated using wafer-level microfabrication. Also, it will be appreciated that the following electrode characteristics, for example, but not limited to, number, distribution (e.g., pitch), diameter, and material can be modified as well.

As noted above, the probe body 22 is preferably made from a polymer, and more preferably from a flexible, biocompatible polymer such as polyimide, parylene, silicones, etc. Additionally, the size, number, configuration and location of the probes 20 of each probe subsystem 16 can be tailored for specific applications. Lastly, the form factor of the system 10, and particularly the substrate 12 with the culture wells 18 and the probe subsystems 16 attached thereto, can easily be modified to fit specific electronic hardware systems (i.e., electrophysiological recording/stimulation systems), accommodate various connectors for external wiring, or meet another specification for size based on cell culture requirements (e.g., volume of hydrogel, volume of cell culture media, number of cells, etc.). Using the as-designed location of the electrodes 30 within each array prior to actuation, combined with measured angle data of the actuated probes 20, a unique electrode map in 3D space can be generated for each probe array.

Once the probes 20 are actuated, the cell culture well 18 is adhered to the upper surface 12a of the substrate 12 surrounding the vertically arranged array of probes 20 of at least one of the probe subsystems 16. Dissociated cells (e.g., neuronal cells, cardiac cells) mixed with a hydrogel (e.g., collagen) or other 3D culture matrix can then be added to the cell culture well 18. As the hydrogel polymerizes and solidifies, the 3D distribution of the cells is maintained. Thus, cells are distributed around the electrodes 30 of the probes 20 in the X, Y, and Z planes and the networks are formed around the electrodes. Maturation of the cells over days or weeks results in electroactive function that can be measured and recorded in a non-invasive manner using the probe subsystems 16 of the system 10 and compatible electronic instrumentation. Alternatively, spheroids or organoids consisting of electroactive cells may be formed in situ within the culture well 18, thus forming cellular complexes around the actuated probes 20, allowing for subsequent non-invasive recording or stimulation of the 3D cell constructs. The probe 20 stiffness can be modulated such that a pre-formed organoid or cell-hydrogel construct could be placed on the actuated probe 20 array such that the probe bodies penetrate the matrix of cells and can record or stimulate inside the volume of cells.

At Lawrence Livermore National Laboratory, the system 10 is currently being used by the co-inventors to form a 3D "Brain-on-a-Chip" device for countermeasure validation, drug development, and neurological disease research. The work of the co-inventors has thus far specifically used rodent or human-derived neurons and neuroglia (e.g., astrocytes and oligodendrocytes) suspended in a 3D hydrogel matrix. Three-dimensional neuronal cultures more accurately recapitulate in vivo architecture and function on the system 10, enhancing the quality of in vitro data obtained on these organ platforms, especially compared to 2D neuronal cultures. Advantageously, the system 10 facilitates the recording of neuronal activity in 3D space (i.e., within the 3D volume defined by the culture well 18), as the electrodes 30 are distributed preferably uniformly in each of the X, Y, and Z planes.

After actuation of the array of the probes 20 of the probe subsystem 16, the cell-containing solution is pipetted into the three culture wells 18 of the system 10, then subsequently cured at or near 37° C. to form a cross-linked matrix of cells from which the electrodes 30 in 3D space can record. Each culture well 18 in this example contains an array of ten probes, each containing eight electrodes 30. The probes 20 may vary in length and width, but in this example each is 1100 μm in length and 90 μm in width. The form factor of the system 10, as well as the position and size of the electrical interconnection pads 14 bordering the perimeter of the substrate 12, allow the system 10 to interface with a suitable electronic instrumentation/recording devices for the recording of electrical signals detected by the probes, or the application of electrical signals using the probes 20. In one example, a commercial headstage available from Multi Channel Systems GmbH (MCS) of Reutlingen, Germany, may be used as the commercial headstage. Pogo pins in the headstage lid contact the electrical connection pads 14 to make the electrical connection with each of the electrodes 30 on each of the probes 20.

The system 10 has successfully sustained viable and functional human iPSC-derived neuronal cells and primary rat neurons for over 45 days in vitro (DIV). Additionally, action potential events have been recorded from multiple electrodes within each array at several different time points over the course of multiple weeks.

The system 10 of the present disclosure is expected to have a number of important uses including, but not limited to, research involving neuronal communication in 3D, 3D peripheral nervous system (PNS) platforms, drug development, countermeasure validation, chemical exposure response of electroactive cells in 3D, real-time chemical sensing (oxygen, neurotransmitters, pH, etc.), disease research (Alzheimer's, Parkinson's, epilepsy, Traumatic Brain Injury, etc.), recording/stimulation of spheroids/organoids, recording/stimulation of cardiac cells, and microfluidic delivery of chemicals in 3D.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A biocompatible, in vitro probe system comprising:
a substrate;
a culture well supported on the substrate and defining a three-dimensional volume for containing in vitro cultures of electroactive cells;
at least one probe subsystem supported on the substrate and including at least one probe having an array of electrodes, the probe being disposed within the culture well for in vitro electrically communicating with the electroactive cells, and adapted to be interfaced to an external electronic instrumentation/recording device;
the probe further including a first region, a second region and a hinge region including a void forming an engineered weakness for controllably weakening the probe at a selected location to aid in bending the probe during a manufacturing operation, the second region including the electrodes and forming a probe sensing body portion, and the first region being fixed to the substrate and adapted to be placed in electrical communication with the external electronic instrumentation/recording device; and
the electrodes being spaced elevationally apart along the second region at different distances from the first region.

2. The system of claim 1, wherein the probe subsystem includes a plurality of the probes, with each one of the probes having a plurality of electrodes thereon.

3. The system of claim 1, wherein the probe subsystem includes a plurality of the probes, with each said probe having a plurality of the electrodes thereon spaced apart from one another in a straight line.

4. The system of claim 3, wherein each said probe of the probe subsystem includes a first region and a second region, with the second region including the plurality of electrodes, wherein each one of the second regions is disposed non-parallel to the first regions within the three-dimensional volume of the culture well.

5. The system of claim 3, wherein the probes are arranged to extend non-parallel to the substrate, such that the probes collectively form an X-Y spatial arrangement of probes within the culture well, and such that the electrodes of the probes are arranged in X, Y and Z planes within the three-dimensional volume of the culture well.

6. The system of claim 5, wherein the probes are arranged to extend generally orthogonal to the substrate, and parallel to one another, within the three-dimensional volume of the culture well.

7. The system of claim 1, further comprising at least one electrical connection pad disposed on the substrate and in electrical communication with the probe subsystem.

8. The system of claim 1, wherein the probe subsystem is used to apply an electrical signal to the electrode.

9. The system of claim 1, wherein the electrode of the probe subsystem is used to receive electrical signals generated within the cultures of electroactive cells.

10. The system of claim 1, wherein the probe subsystem is used to both apply electrical signals to the electrode and to receive electrical signals from the electrode.

11. The system of claim 1, wherein the culture well is secured to an upper surface of the substrate by a biocompatible epoxy.

12. A biocompatible, in vitro probe system comprising:
a planar substrate;
a culture well secured to a surface of the substrate and defining a three-dimensional volume for containing in vitro cultures of electroactive cells;
at least one probe subsystem supported on the substrate and including a first region, a second region and a third region located between the first region and the second region;
the second region including a plurality of probes arranged in an X-Y plane extending non-parallel to the first region, and disposed inside the three-dimensional volume of the culture well;
at least a portion of the first region extending parallel to the substrate and out from the culture well;
the third region including a void forming an engineered weakness in the substrate to facilitate bending of the probe at the third region;
each of the probes including a plurality of elevationally spaced apart electrodes arranged at different distances from the first region that collectively form an in vitro, three-dimensional network of electrodes within the three-dimensional volume of the culture well; and
the probe subsystem including circuit traces extending from the first region into the second region and into electrical contact with the electrodes of each of the probes, for enabling an external electrical subsystem to electrically communicate with the electrodes on the probes.

13. The probe system of claim 12, further comprising a plurality of independent electrical connection pads secured to the surface of the substrate, and in electrical communication with the circuit traces, the electrical connection pads being adapted for connection to the external electrical subsystem.

14. The probe system of claim 13, wherein each one of the electrical connection pads is independently coupled to a single one of the circuit traces, to enable each one of the electrical connection pads to independently communicate with an associated one of the electrodes.

15. The probe system of claim 12, wherein the probe subsystem is configured to at least one of:
apply an electrical signal to at least one of the electrodes; and
receive electrical signals from at least one of the electrodes.

16. The probe system of claim 12, wherein the probes define a X-Y spatial arrangement of probes, with the electrodes defining a three-dimensional network of electrodes within the three-dimensional volume of the culture well.

17. A method for electrically communicating with a quantity of cultures of electroactive cells, comprising:

using a culture well to define a three-dimensional volume for containing in vitro cultures of electroactive cells;

using at least one probe subsystem having a portion with a plurality of probes extending into the culture wells, wherein each said probe includes a first region supported from a planar substrate, a second region extending non-parallel to the first region, and a third region separating the first region and the second region, the third region including a void to form an engineered weakness in the probe to permit the second region to be bent to extend non-parallel to the first region;

the second region including a plurality of elevationally spaced apart electrodes disposed at different distances from the first region, to form a three-dimensional network of electrodes within the three-dimensional volume of the culture well; and using the electrodes to in vitro electrically communicate with the electroactive cells.

18. The method of claim 17, further comprising interfacing the at least one probe subsystem to an external electrical subsystem for at least one of applying electrical signals to at least one of the electrodes, or receiving electrical signals from at least one of the electrodes.

\* \* \* \* \*